United States Patent [19]

Sharpe et al.

[11] Patent Number: 4,832,491
[45] Date of Patent: May 23, 1989

[54] METHOD OF AND APPARATUS FOR SPECTROSCOPICALLY ANALYZING SAMPLES

[75] Inventors: Michael R. Sharpe, Newton; Stephen J. Cooke, Royston, both of England

[73] Assignee: U.S. Philips Corporation, New York, N.Y.

[21] Appl. No.: 61,239

[22] Filed: Jun. 10, 1987

[30] Foreign Application Priority Data

Jun. 16, 1986 [GB] United Kingdom ................ 8614583

[51] Int. Cl.$^4$ ......................... G01J 3/32; G01N 21/27
[52] U.S. Cl. .................... 356/326; 250/214 C
[58] Field of Search ............ 250/214 C; 356/319, 356/323, 325, 326, 418

[56] References Cited

U.S. PATENT DOCUMENTS 3,727,066  4/1973  Louderback et al. .......... 350/214 C
4,687,333  8/1987  Odasima et al. .................... 356/418

Primary Examiner—Vincent P. McGraw
Attorney, Agent, or Firm—Paul R. Miller

[57] ABSTRACT

A single beam wavelength scanning spectrophotometer comprises means for passing radiation from a radiation source (1) to a radiation detector (4) over a defined path which includes a monochromator (2) capable of being scanned across a selected wavelength range, means (7) for storing a first set of signals representative of the radiation falling on the radiation detector, the first set of signals being spread across the selected wavelength range to form a first spectral response, means for inserting a sample (3) in the defined path, means for producing a second set of signals representative of the radiation falling on the radiation detector when the sample (3) is inserted in the defined path, the second set of signals being spread across a selected wavelength range to form a second spectral response, and means (7) for calculating the transmittance or absorbance of the sample at desired wavelengths from the first and second spectral responses. The ambient temperature in the region of the radiation detector (5) is monitored (6) and the first and/or second sets of signals are modified in dependence on the ambient temperature when the first and second set of signals are produced.

23 Claims, 5 Drawing Sheets

METHOD OF AND APPARATUS FOR SPECTROSCOPICALLY ANALYZING SAMPLES

DESCRIPTION

The invention relates to a method of analysing one or more samples in succession using a single beam wavelength scanning spectrophotometer comprising the steps of (1) passing radiation from a radiation source to a radiation detector over a defined path which includes a wavelength selective element capable of being scanned across a selected wavelength range, (2) storing a first set of signals representative of the radiation falling on the radiation detector with the first set of signals being spread across the selected wavelength range to form a first spectral response, (3) inserting a sample in the defined path, (4) producing a second set of signals representative of the radiation falling on the radiation detector when the sample is inserted in the defined path with the second set of signals being spread across a selected wavelength range to form a second spectral response (5) calculating the absorbance or transmittance of the sample at desired wavelengths using the first and second spectral responses, and (6) repeating steps (3) to (5) for each successive sample.

The invention further relates to a single beam wavelength scanning spectrophotometer comprising means for passing radiation from a radiation source to a radiation detector over a defined path which includes a wavelength selective element capable of being scanned across a selected wavelength range, means for storing a first set of signals representative of the radiation falling on the radiation detector with the first set of signals being spread across the selected wavelength range to form a first spectral response, means for inserting a sample in the defined path, means for producing a second set of signals representative of the radiation falling on the radiation detector when the sample is inserted in the defined path with the second set of signals being spread across a selected wavelength range to form a second spectral response and means for calculating the transmittance or absorbance of the sample at desired wavelengths from the first and second spectral responses.

The detector output of a single beam spectrophotometer varies rapidly with wavelength as it depends on the combined effects of the variation with wavelength of the source energy, grating efficiency, mirror reflectivity and detector photo-sensitivity. This means that a spectrum can only be obtained from simple single beam instruments by the tedious process of setting a baseline detector output with either a clear optical path or when analysing samples dissolved in a solvent in a cell containing the solvent (blank or reference solution) in the optical path, moving the sample cell into the beam, measuring the detector output, ratioing the detector outputs to calculate absorbance or transmittance of the sample, changing the wavelength, and repeating the process for each data point required.

Linking a computer to the spectrophotometer can take the tedium out of this process and produce the data faster than any operator. The computer is simply told the start and stop wavelengths of the scan and the blank is placed in the beam. The computer then commands the spectrophotometer to drive to the start wavelength and to store the detector output in its memory. It then commands the spectrophotometer to go to the next wavelength and the process is repeated until the spectrum of the blank solution (and the cell containing it) is held in its memory. The blank solution is then emptied and the cell refilled with the sample solution and placed in the beam. The measurement sequences are repeated and at each wavelength the stored detector output when using the blank is ratioed by the computer with the new reading to yield the net absorbance or transmittance of the sample which is then displayed and plotted.

This principle of storing a spectrum of the blank and ratioing it with subsequent sample spectra has, with the reducing costs of memory and processing power, now become a practicable proposition for purposely built single beam scanning instruments. Such an instrument is currently manufactured and sold by Pye Unicam Limited under the type reference PU8600. However, the technique does have its limitations as it demands a high level of stability with time, both of the instrument and of the sample matrix. Little is gained if the instrumental readings drift between the time when the blank was measured and when the last sample is run. Similarly, if blanks and samples exhibit absorbance changes in time due to settling of particulate matter, variations in ambient temperature, sensitivity to light, etc., then the recorded differences will not be true. All electronic circuits drift, especially when warming to operating temperature. Consequently single beam scanning instruments tend to be left powered-up night and day with only motors and sources shut-down when the instrument is not in use (reasonable in a laboratory carrying out routine analyses but unwise in research laboratories with patchy and unpredictable instrumental usage). Scanning rapidly has been the only way of reducing the vulnerability to temporal changes in the sample. However, this involves other performance compromises and any apparent throughput gains are quickly swallowed by the necessity to produce hard-copy after the scan rather than simultaneously. Therefore, single beam scanning spectrophotometers have currently been confined to applications where low to medium performance is acceptable. For the highest levels of performance the double beam instruments have been used.

It is an object of the invention to enable the use of a single beam scanning spectrophotometer while mitigating the effects of one or more of the disadvantages discussed hereinbefore.

The invention provides a method of analysing one or more samples in succession using a single beam scanning spectrophotometer as set forth in the opening paragraph characterised by the further steps of (7) monitoring the ambient temperature in the region of the radiation detector, and (8) modifying the firs and/or second sets of signals in dependence on the ambient temperature when the first and second set of signals are produced.

By monitoring the ambient temperature in which the radiation detector is operating changes in detector sensitivity with ambient temperature may be compensated for and the time between calibrations of blank solution absorbance spectra increased.

The first and second sets of signals may be modified by passing them through a circuit arrangement having a temperature co-efficient of gain of substantially the same magnitude but of opposite sign to the temperature co-efficient of sensitivity of the radiation detector.

Alternatively the method may further comprise the steps of measuring the ambient temperature at a first instant immediately prior to, immediately subsequent t9, or during the period during which the first set of signals is generated, storing the temperature measured at the first instant, measuring the ambient temperature at a second instant immediately prior to, immediately subsequent to, or during the period i which the second set of signals is produced, and modifying the first or the second set of signals in accordance with the difference in ambient temperature between the first and second instants in such a manner as to compensate for changes in radiation detector sensitivity with temperature.

In a further alternative the method may further comprise the steps of measuring the ambient temperature at a first instant immediately prior to, immediately subsequent to, or during the period during which the first set of signals is generated, modifying the first set of signals in dependence on the difference in ambient temperature measured at the first instant and a predetermined temperature measuring the ambient temperature at a second instant immediately prior to, immediately subsequent to, or during the period in which the second set of signals is produced, and modifying the second signals in dependence on the difference in ambient temperature measured at the second instant and said predetermined temperature.

The selected wavelength range in step (2) may be the same as the selected wavelength range in step (4). The method may further comprise displaying the calculated absorbance or transmittance of the sample. The calculated absorbance or transmittance may be converted to concentration for display.

The invention further provides a single beam wavelength scanning spectrophotometer as set forth in the second paragraph characterised by means for monitoring the ambient temperature in the region of the radiation detector and means for modifying the first and/or second sets of signals in dependence on the ambient temperature when the first and second set of signals are produced.

The modifying means may comprise a temperature sensitive element located in the region of the radiation detector with the temperature sensitive element being arranged to modify the gain of an amplifier to the input of which the output of the radiation detector is connected in such a manner that the gain of the amplifier varies in an inverse manner to that of the output of the radiation detector with changes in ambient temperature.

Alternatively the monitoring means may comprise means for measuring the temperature at a first instant immediately prior to, immediately subsequent to, or during the period during which the first set of signals is generated, means for storing the temperature measured at the first instant, and means for measuring the ambient temperature at a second instant immediately prior to, immediately subsequent to, or during the period in which the second set of signals is produced, and the modifying means comprises means for modifying the first or the second set of signals in accordance with the difference in ambient temperature between the first and second instants in such a manner as to compensate for changes in radiation detector sensitivity with temperature.

In a further alternative the monitoring means may comprise means for measuring the temperature at a first instant immediately prior to, immediately subsequent to, or during the period during which the first set of signals is generated, and means for measuring the ambient temperature at a second instant immediately prior to, immediately subsequent to, or during the period in which the second set of signals is produced, and the modifying means comprises means for modifying the first set of signals in dependence on the difference between the ambient temperature measured at the first instant and a predetermined temperature and means for modifying the second set of signals in dependence on the difference between the ambient temperature measured at the second instant and the predetermined temperature.

The selected wavelength range for the first set of signals may be the same as the selected wavelength range for the second set of signals.

The spectrophotometer may comprise means for displaying absorbance or transmittance of the sample. The spectrophotometer may comprise means for converting the calculated absorbance or transmittance to concentration for display.

Embodiments of the invention will now be described, by way of example, with reference to the accompanying drawings, in which.

Figure 1:
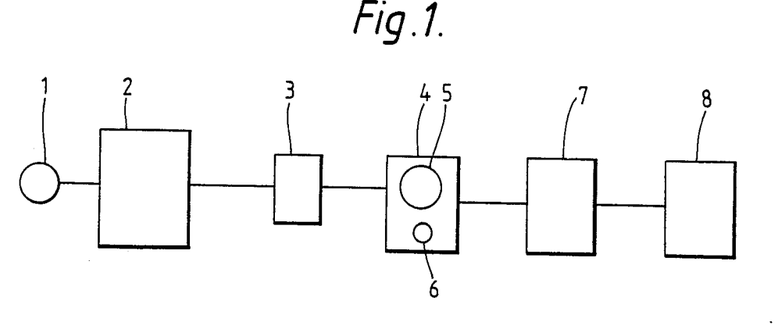
FIG. 1 shows in block schematic form a spectrophotometer according to the invention.

FIG. 1 shows in block schematic form a single beam wavelength scanning spectrophotometer comprising a radiation source 1, the radiation from which is directed to a monochromator 2 and thereafter passes through a sample cell 3 before falling on a radiation detection unit 4. The radiation detection unit 4 comprises a radiation detector device 5, such as a photomultiplier tube or a photodiode, which produces an electrical signal representative of the radiation falling on it and a temperature sensor 6, such as a thermistor, which is placed so as to sense the ambient temperature in which the radiation detector 5 is operating. The output of the device 5 is passed to a signal processing circuit 7 either directly or after modification in dependence on the sensed temperature. If the output of the radiation detector 5 is passed directly to the signal processing circuit 7 then a signal representative of the sensed temperature is also passed to the signal processing circuit 7. The output of the signal processing circuit 7 is fed to a display unit 8 which may be of any convenient form, for example, an alpha numeric display, a video display unit, or if a hard copy of the results is required a cart recorder or printer.

In operation the sample cell 3 is first filled with a blank solution, e.g. the solvent in which the sample is to be dissolved, the monochromator is scanned between pre-selected wavelength limits and the output of the radiation detector with the sample cell 3 inserted in the optical path is measured at intervals across the wavelength range. The measured output signals are stored within the processing circuit 7. The number of intervals is arbitrary and will depend on the amount of storage provided in the processing circuitry 7 and the wavelength resolution required. The ambient temperature in the region of the radiation detector 5 is sensed by the sensor 6 and the output of the radiation detection unit 4 may be modified in dependence on the temperature sensed. Alternatively the temperature sensor 6 may also produce a signal which is fed to the processing circuitry 7 which may then include means for modifying the received signal from the radiation detector 5 in dependence on the signal received from the temperature sensor 6. In the latter case it will be necessary also to store the signal representing the ambient temperature. As a further alternative the processing circuitry 7 may be arranged to normalise the received signal to that which would be produced at a reference temperature, in which case it is not necessary to store the signal representative of the sensed ambient temperature.

A sample cell 3 containing a sample is then placed in the radiation path and the monochromator 2 is caused to scan a desired wavelength range, either the same as or part of the previous range, and the radiation received by the radiation detection unit 4 is measured and processed by the processing circuit 7. The ambient temperature in the region of the radiation detector 5 is sensed by the temperature sensor 6 and the output of the radiation detector 5 is either modified in dependence on the sensed ambient temperature or a measure of the temperature is passed to the processing circuit 7 together with the output of the radiation detector 5. In the latter case either the stored values of radiation detector output are corrected for the change in temperature between measurement of the blank and sample solutions or the sample values are corrected. When the further alternative is adopted the sample values are normalised to the reference temperature using the measured ambient temperature when the sample values are generated. Subsequently the processing circuitry calculates the transmittance or absorbance of the sample from the stored and sample radiation signals and causes them to be passed to the display unit 8. If the output of the radiation detector 5 is modified in the radiation detection unit 4 then it is not subsequently corrected in the processing circuitry 7.

The foregoing description has assumed that the sample to be analysed is dissolved in a solvent. However, as is well known to those skilled in the art, spectroscopic analysis may be applied to solid samples, for example filter glasses, or to liquid substances which are themselves the samples and are not dissolved in a solvent. In the former case the initial scan is made with no sample in the radiation path i.e. the path is completely clear, while in the second case an empty sample cell is inserted in the radiation path for the initial scan.

In this way the disadvantage of changing response of single beam scanning instruments due to changing sensitivity of the radiation detector with temperature changes can be significantly reduced. This allows longer intervals between calibration and enables the instrument to be used with a much shorter "warm-up" period.

Figure 2:
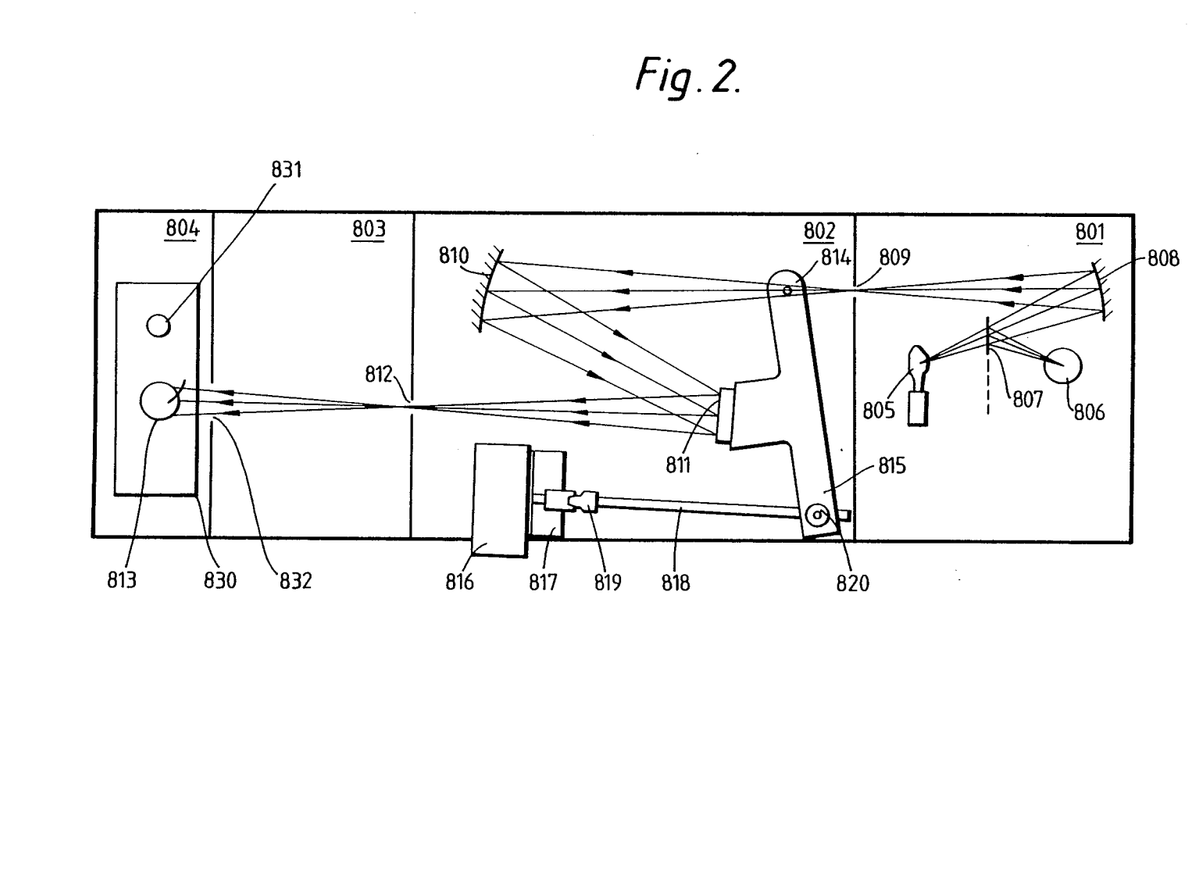
FIG. 2 is a plan view of the optical layout of a spectrophotometer according to the invention.

FIG. 2 shows the layout of a spectrophotometer having a Gillieson Monochromator. The spectrophotometer comprises a first section 801 which includes a source of radiation, a second section 802 housing the monochromator, a third section 803 in which the sample to be analysed is placed, and a fourth section 804 which includes a radiation detector.

The spectrophotometer shown includes a tungsten filament lamp 805 and a deuterium lamp 806 to enable a wavelength range which covers both the visible and ultra violet regions of the spectrum to be covered. A mirror 807 is movable between a first position (as shown) in which radiation from the deuterium lamp 806 is reflected onto a concave mirror 808 and a second position (shown dotted) in which radiation from the tungsten lamp 805 is allowed to fall on the concave mirror 808.

Radiation reflected from the concave mirror 808 is focussed on an entrance slit 809 of the monochromator 802 and passes through the entrance slit to fall onto a concave mirror 810. The radiation is reflected by the mirror 810 as a converging beam onto a diffraction grating 811 where it is diffracted and focussed on an exit slit 812 of the monochromator 802. The radiation then passes through the sample compartment 803 and falls on a detector 813 which may, for example, be in the form of a photomultiplier tube, a vacuum photo tube or a photo diode in the fourth section 804. The electrical output of the detector 813 is fed to signal processing circuitry (not shown in FIG. 2) which converts it into suitable form for display. In order to cause the radiation passing through the sample compartment 803 to scan a selected wavelength range the diffraction grating is rotated about an axis perpendicular to the plane of the drawing and passing through the center of a pivot 814. This is achieved by rotating the arm 815 which carries the grating 811 about the pivot 814.

A stepper motor 816 is mounted on a bracket 817 in the monochromator 802 and its output is coupled to a threaded shaft 818 by a universal joint 819. A nut 820 is pivotally mounted in an aperture in the arm 815 and rides on the shaft 818. Thus as the motor 816 steps the shaft 818 rotates and the nut 820 advances along the threaded shaft causing the arm 815 to rotate about the pivot 814.

The radiation beam passes over the top of the pivot 814. It is, of course, necessary to arrange the entrance and exit slits, mirror 810 and diffraction grating 811 in appropriate orientation to be in the radiation path and to enable that path to pass over the pivot 814.

Within the fourth section 804 the radiation detector 813 is mounted on a printed circuit board 830 which also carries a temperature sensor 831. Thus the ambient temperature within the further section, which is preferably fully enclosed apart from an aperture 832 to enable radiation from the monochromator exit slit 812 to fall on the detector 813 after passing through the sample, is sensed by the temperature sensor 831 and can be used either directly to modify the radiation detector output before it is passed to the signal processing circuitry or can be modified in the processing circuitry if a signal representative of the ambient temperature is passed to the signal processing circuitry.

Figure 3:
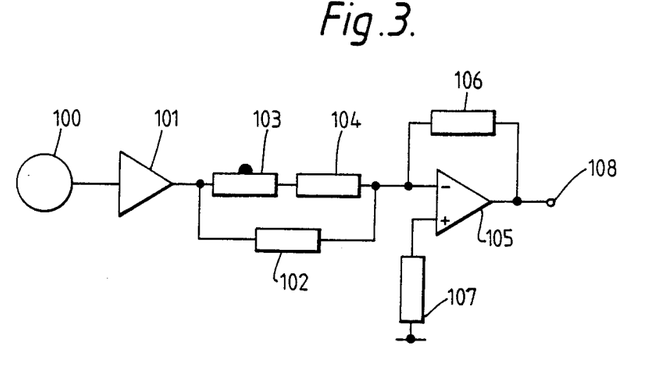
FIG. 3 is a circuit diagram of one embodiment of the radiation detection unit shown in FIG. 1.

FIG. 3 shows an arrangement for modifying the output signal produced by the radiation detector in dependence on the ambient temperature in which the radiation detector is operating. The arrangement comprises a radiation detector 100 in the form of a photomultiplier tube whose output is connected to the input of an amplifier 101. The radiation detector 100 is equivalent to the radiation detector device 5 of FIG. 1. The output of the amplifier 101 is connected to the one end of a network comprising a resistor 102 connected in parallel with the series arrangement of a thermistor 103 and a resistor 104. The thermistor 103 is an embodiment of the temperature sensor 6 of FIG. 1. The other end of the network is connected to an inverting input of an amplifier 105 which has a feedback resistor 106 connected between its output and inverting input. A further resistor 107 is connected between a non-inverting input of the amplifier 105 and ground while the output of the amplifier 105 is connected to the output 108 of the arrangement.

In this example the photo multiplier tube is a multi alkali photocathode photomultiplier as sold by Hamamatsu TV Co. Limited. For these devices the temperature co-efficient of sensitivity over the wavelength range of 200 nm to 800 nm is almost constant at −0.4% per °C. The arrangement shown in FIG. 3 includes an amplifying circuit having a temperature co-efficient of gain equal and opposite to that of the photomultiplier 100. Amplifier 101 forms a current-voltage preamplifier while the circuit to which its output is connected forms a modifying circuit which has a temperature co-efficient of gain of +0.4% per °C. In this example amplifier 105 is a high gain operational amplifier and the thermistor 103 is a disc type thermistor with a negative temperature co-efficient of resistance of −4.9% per °C and a resistance of 33K ohms at 25 °C. The values of resistors 102, 104, 106 and 107 were 7.8K Ohms, 18.7K Ohms, 6.8K Ohms and 3.3K Ohms, respectively. The characteristics of the arrangement would, of course, be modified to adapt to the properties of different radiation detectors.

Figure 4:
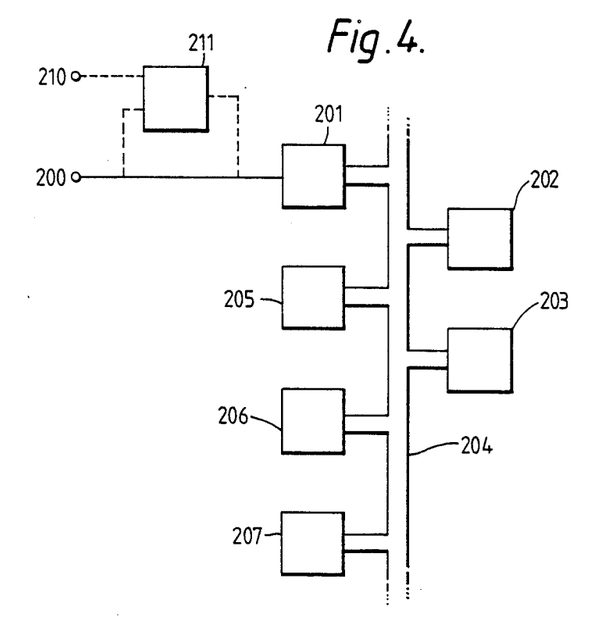
FIG. 4 is a block schematic diagram of one embodiment of the signal processing circuit shown in FIG. 1, and FIGS. 5, 6 and 7 show flow diagrams illustrating a method of sample analysis according to the invention.

FIG. 4 shows in block schematic form the signal processing circuit 7 of the spectrophotometer shown in FIG. 1 together with circuitry for controlling the operation of the instrument. The signal processing circuit has an input 200 to which the output 108 of the arrangement shown in FIG. 3 may be connected, i.e. the input 200 receives the output signal from the radiation detection unit 4. This signal is converted into digital form by an analogue to digital converter (ADC) 201. The signal processing circuitry further comprises a microprocessor 202 and a memory 203 which are interconnected with the ADC 201 by means of a bus 204. Also connected to the bus 204 are a keyboard unit 205 by means of which an operator can enter appropriate operating instructions, for example wavelength range, scanning speed, number of samples, form of output, a display unit 206, for example chart recorder, printer, VDU, and a control interface unit 207 through which appropriate signals are passed from the microprocessor 202 for causing the monochromator 2 to scan across the selected wavelength range and from various elements within the instrument information to the microprocessor 202 to enable it to generate the appropriate control instructions.

Figure 5:
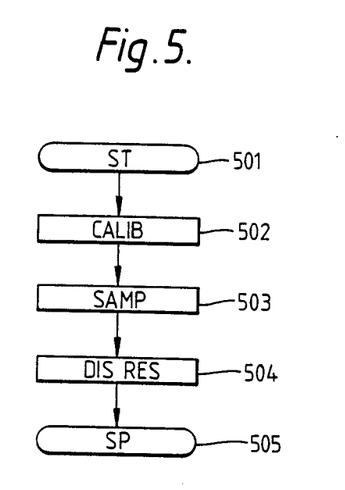

FIG. 5 is a flow diagram illustrating a method of analysis according to the invention.

Box 501 (ST) represents the start of the analysis i.e. the switching on and initial setting up of the instrument. The step represented by box 502 (CALIB) is a calibration scan which comprises inserting a sample cell containing a blank solution in the optical path, running a wavelength scan and storing the results. The step represented by box 503 (SAMP) is a sample scan comprising inserting a sample cell containing the sample dissolved in the blank solution in the optical path, running a wavelength scan, calculating the absorbance or transmittance of the sample from the results of the current scan and the calibration scan. The box 504 (DIS.RES) represents the presentation of the results of the analysis, for example the variation of absorbance or transmittance with wavelength, to an output device such as a chart recorder or a VDU. This may be done either after the completion of the sample scan or simultaneously with the sample scan as the values at each wavelength step become available. The box 505 (SP) marks the completion of the analysis.

As discussed earlier with respect to FIG. 1 solid samples or liquid samples which do not contain dissolved samples may be analysed using the appropriate procedures for producing the calibration scan.

Figure 6:
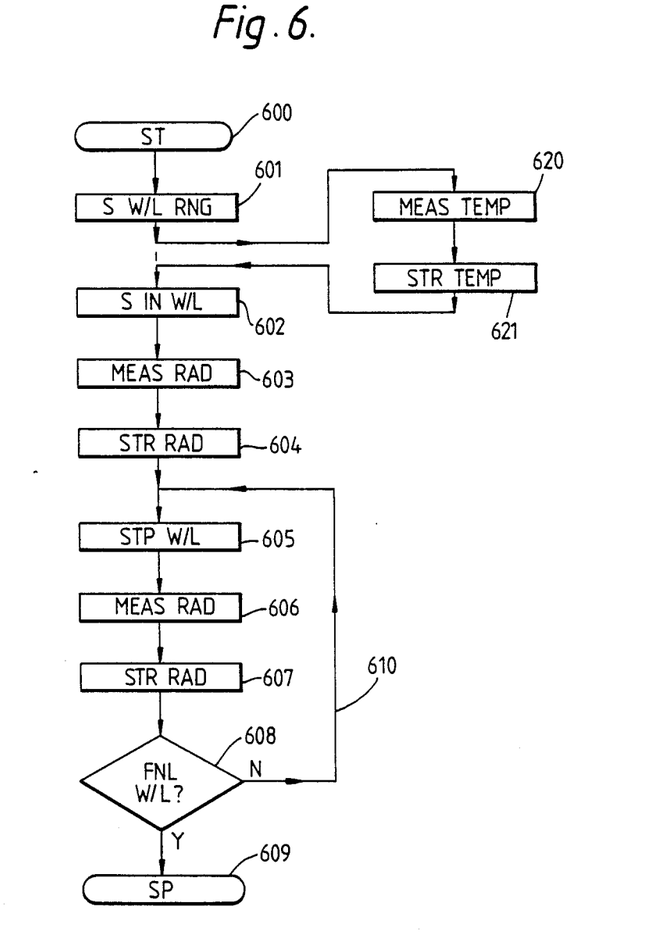

FIG. 6 is a flow diagram illustrating the steps taken in one implementation of the calibration scan represented by box 502 of FIG. 5. Box 600 (ST) represents the entry into this part of the method. Box 601 (SET W/L RNG) represents an input from the keyboard 205 which defines the upper and lower limits of the range of wavelengths over which the monochromator 2 is to be scanned. The microprocessor 202 takes this information and uses it to provide appropriate driving signals to the monochromator 2 through the control interface circuit 207 to drive the monochromator to the initial wavelength of the scan range, box 602 (S.IN W/L). The microprocessor then causes the output of the radiation detector to be digitised by the analogue to digital converter to produce a digital value representative of the magnitude of the radiation falling on the detector, box 603 (MEAS RAD). This value is then stored in the memory 203 at a location determined by the wavelength setting of the monochromator, box 604 (STR RAD). The microprocessor 202 then produces an instruction, which is fed via the control interface unit 207 to the monochromator, which causes the monochromator to step to an adjacent wavelength, box 605 (STP.W/L). Subsequently the output of the radiation detector is digitised by the analogue to digital converter, box 606 (MEAS RAD) and the digital value is stored in a location of memory 203 associated with the present wavelength to which the monochromator is set, box 607 (STR RAD). A decision is then taken, box 608 (FNL W/L?), as to whether the monochromator has stepped to the final wavelength, that is it has scanned across the complete wavelength range selected. If it has then the process ends, box 609 (SP), and the instrument is ready for a sample to be inserted into the radiation beam to allow its characteristics to be determined. If the monochromator has not completely scanned the selected wavelength range then path 610 is followed and the steps represented by boxes 605 to 608 are repeated until the wavelength scan has been completed.

Figure 7:
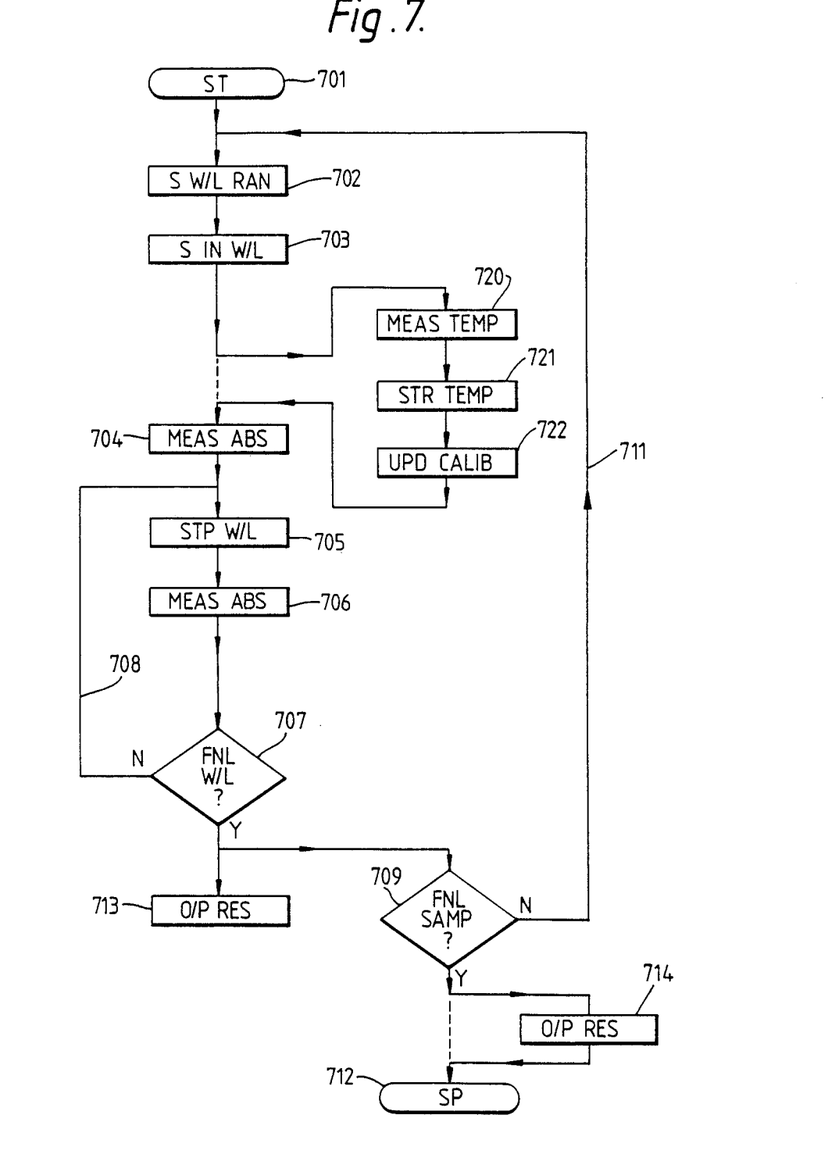

FIG. 7 is a flow diagram illustrating the steps taken in one implementation of the sample scan represented by box 503 of FIG. 5. Box 701 (ST) represents the start of the procedure while box 702 (S.W/L RAN) represents the setting of the wavelength range over which the sample scan is to take place. This may take the form of information entered into the microprocessor 202 by an operator using the keyboard 205 and may include both the limits of the wavelength range of the scan and the increments by which the monochromator steps i completing the scan, i.e. the wavelength intervals at which measurements are taken. The microprocessor then generates an instruction to cause the monochromator to drive to its initial wavelength setting, box 703 (S.IN.W/L). This instruction is passed to a stepper motor in the monochromator which causes a diffraction grating to rotate by a given amount, the instruction being converted to an appropriate driving signal by the control interface circuit 207. The output of the detector is then digitised by the analogue to digital converter 201, this time with a sample inserted in the optical path i.e. the sample cell 3 contains a sample dissolved in the solvent used for the calibration scan, and the absorbance or transmittance of the sample is calculated by use of the stored digitised signal obtained in the calibration scan and the just obtained digitised signal, box 704 (MEAS ABS). The calculated value may then be fed to a display device or may be stored in memory for later display. The microprocessor then generates an instruction to cause the monochromator to step to the next wavelength, box 705 (STP W/L), the magnitude of the steps may be pre-programmed and constant or may be controllable by entry of information by the operator, for example using the keyboard. The signal produced by the radiation detector at the new wavelength is then digitised and used together with the stored calibration value to calculate the absorbance or transmittance, box 706 (MEAS ABS). Again the calculated value may then be fed to the display device or stored in memory for later display. The microprocessor then checks whether the monochromator has stepped to the final wavelength, box 707 (FNL W/L?), and if not then the path 708 is taken and the monochromator is stepped to the next wavelength. If the final wavelength has been reached the microprocessor may then check whether another sample is to be analysed, using an automatic sample changer, box 709 (FNLSAMP?), and if so then path 711 is followed. If no further sample is to be analysed then the process ends box 712 (SP). If the results are stored in memory then when the final wavelength of a scan is reached the resulting absorbance or transmittance scan may be fed to a display device. This may take place either at the end of each sample scan box 713 (O/PRES) or at the end of the analysis of a plurality of samples box 714 (O/PRES).

The procedure described hereinbefore with reference to FIGS. 5 to 7 is appropriate when the radiation detection unit 4 takes the form shown in FIG. 3, that is the output of the radiation detection unit 4 is made substantially constant with ambient temperature variations by means of a compensation circuit including a temperature sensing element. It is alternatively possible to correct for the temperature co-efficient of sensitivity of the photomultiplier tube, or other detector, within the microcomputer circuit shown in FIG. 4. In this case the output of the amplifier 105 (FIG. 3) would be fed to the input 200 (FIG. 4) while an output signal representative of the ambient temperature in the region of the radiation detector would be fed to an input 210. The input 200 is then fed to a first input of a multiplexer 211 while the input 210 is fed to a second input of the multiplexer 211. The output of the multiplexer 211 is fed to the analogue to digital converter 201 in place of the input 200.

The previously described flow diagram in FIG. 6 is now modified in that the ambient temperature in the region of the radiation detector is measured and stored in the memory for subsequent use during the measurement scan. In one scheme illustrated in FIG. 6 after the step represented by box 601 (SET W/L RNG) of setting the wavelength range over which the scan is to be performed the microprocessor 202 causes the control interface unit 207 to produce signals which cause the multiplexer 221 to select input 210 and apply the signal thereat to the analogue to digital converter 201. The ADC 201 digitises this signal which represents the ambient temperature in the region of the radiation detector, box 620 (MEAS TEMP). The microprocessor 202 then causes the digitised signal to be stored in memory 203, box 621 (STR TEMP). The digitised signal may be processed before being stored by the microprocessor if necessary. If desired the temperature may be continuously monitored during the calibration scan and a temperature reading stored at each wavelength setting during the scan. However, this is not normally necessary as the ambient temperature is unlikely to change significantly during a scan at any normally used scanning rate. Clearly the instant at which the temperature is sensed can be at any desired time provided that the temperature does not change significantly between the time that the temperature is sensed and the time at which the calibration scan is run. It is clearly advantageous to sense the temperature at some instant during the scan to give the greatest likelihood that the actual temperature for the whole scanning period is as sensed but provided that the ambient temperature is not changing quickly the temperature sensing could take place prior to or subsequent to the running of the calibration scan.

The previously described flow diagram shown in FIG. 7 is modified in one scheme as follows. When the monochromator has been driven to the initial wavelength the microprocessor causes the multiplexer to select input 210 and feed a signal representative of the ambient temperature in the region of the radiation detector to the analogue to digital converter 201 which produces a digital representation in the bus 204, box 720 (MEAS TEMP). The microprocessor then causes this representation of the temperature to be stored in the memory 203, box 721 (STR TEMP), either in the form received from the output of the analogue to digital converter 201 or after further processing. This value is then used to apply a correction to the calibration scan, box 722 (UPD CALIB), to compensate for the temperature change between the time the calibration scan was made and the time of the current measurement scan. The original calibration scan and temperature may remain stored in the memory 203 or the calibration scan and temperature may be continuously updated as new temperature measurements are made.

Alternatively the calibration scan results may be normalised to a reference temperature and the normalised results stored. The measurement scan is then also normalised to the same reference temperature. This eliminates the need to store the temperature at which the calibration scan takes place since it is not necessary to know the difference in temperature between the times of the calibration and measurement scans as they are normalised to the same temperature.

The correction of the calibration scan may be derived from the characteristics specified in the data sheets for the particular radiation detector, may be derived from a temperature run using a typical detector, or may be derived for each radiation detector when fitted into the instrument by first performing a temperature run and storing the results. The use of the microprocessor for performing the correction of the calibration scan allows a more accurate and flexible correction to be made since the microprocessor can take into account different values of temperature co-efficient at different wavelengths whereas the arrangement shown in FIG. 3 can only compensate for a single value of temperature co-efficient and consequently can only give complete correction if the value of the temperature co-efficient is constant with varying wavelength radiation. This is approximately true for the multialkali photocathode photomultiplier tubes manufactured by Hamamatsu TV Co. Limited which over the wavelength range of 200 to 800 nm have a temperature co-efficient of sensitivity of −0.4% per C.

We claim:

1. A method of analyzing one or more samples in succession with a single beam wavelength scanning spectrophotometer comprising the steps of
   (a) passing radiation from a radiation source to a radiation detector over a defined optical path, said path including a wavelength selective element, said wavelength selective element being scanned over a selected wavelength range,
   (b) storing a first set of signals representative of radiation passing to said radiation detector, said first set of signals being spread over said selected wavelength range to form a first spectral response,
   (c) inserting a sample in said defined optical path,
   (d) producing a second set of signals representative of radiation through said sample to said radiation detector, said second set of signals being spread over a second selected wavelengths range to form a second spectral response,
   (e) calculating absorbance or transmittance of said sample at predetermined wavelengths using said first and second spectral responses,
   (f) repeating said steps (c) through (e) for each successive different sample,
   (g) monitoring ambient temperature in the region of said radiation detector, and
   (h) modifying at least one of said first or said second sets of signals according to ambient temperature when said first and said second sets of signals are produced.

2. A method according to claim 1, wherein said first and said second sets of signals are modified by a circuit providing a temperature coefficient of gain of substantially of the same magnitude but opposite sign to a temperature coefficient of sensitivity of said radiation detector.

3. A method according to claim 1, further comprising the steps of
   (j) measuring said ambient temperature at a first instant of time which is
      (i) immediately prior to a period when said first set of signals is generated, or
      (ii) immediately subsequent to said period when said first set of signals is generated, or
      (iii) during said period when said first set of signals is generated,
   (k) storing measured temperatures at said first instant,
   (l) measuring said ambient temperature at a second instant of time which is
      (i) immediately prior to a period when said second set of signals is produced, or
      (ii) immediately subsequent to said period when said second set of signals is produced, or
      (iii) during said period when said second set of signals is produced, and
   (m) modifying one of said first set of signals or said second set of signals in accordance with a difference in ambient temperature between said first and second second instant of time, said step (m) compensating for changes in sensitivity of said radiation detector with temperature.

4. A method according to claim 3, wherein said selected wavelength range in said step (a) is equivalent to said second selected wavelength range in said step (d).

5. A method according to claim 3, wherein the calculated absorbance or transmittance of said sample obtained in step (e) is displayed.

6. A method according to claim 3, wherein the calculated absorbance or transmittance of said sample obtained in step (e) is converted to concentration for display.

7. A method according to claim 1, further comprising the steps of
   (j) measuring said ambient temperature at first instant of time which is
      (i) immediately prior to a period when said first set of signals is generated, or
      (ii) immediately subsequent to said period when said first set of signals is generated, or
      (iii) during said period when said first set of signals is generated,
   (k) modifying said first set of signals in accordance with a difference in said ambient temperature measured at said first instant of time and a predetermined temperature,
   (l) measuring said ambient temperature at a second instant of time which is
      (i) immediately prior to a period when said second set of signals is produced, or
      (ii) immediately subsequent to said period when said second set of signals is produced, or
      (iii) during said period when said second set of signals is produced, and
   (m) modifying said second set of signals in accordance with a difference in said ambient temperature measured at said second instant of time and said predetermined temperature.

8. A method according to claim 7, wherein said selected wavelengths range in said step (a) is equivalent to said second selected wavelength range in said step (d).

9. A method according to claim 7, wherein the calculated absorbance or transmittance of said sample obtained in step (e) is displayed.

10. A method according to claim 7, wherein the calculated absorbance or transmittance of said sample obtained in step (e) is converted to concentration for display.

11. A single beam wavelength scanning spectrophotometer comprising
    first means for passing radiation from a radiation source to a radiation detector over a defined path, said first means including a wavelength selective element capable of being scanned across a selected wavelength range,
    second means for storing a first set of signals representative of radiation striking said radiation detector, said first set of signals being spread over said selected wavelength range to form a first spectral response,
    third means for inserting a sample in said defined path,
    fourth means for producing a second set of signals representative of radiation striking said radiation detector when said sample is inserted in said defined path, said second set of signals being spread over a second selected wavelength range to form a second spectral response,
    fifth means for calculating transmittance or absorbance of said sample at predetermined wavelengths of said first and second spectral response,
    sixth means for monitoring ambient temperature in the region of said radiation detector, and
    seventh means for modifying at least one of said first and second second sets of signals according to ambient temperature when said first and said second sets of signals are produced.

12. A spectrophotometer according to claim 11, wherein said seventh means comprises a temperature sensitive element in said region of said radiation detector, said temperature sensitive element modifying gain of an amplifier, wherein said radiation detector has an output connected to an input of said amplifier such that said gain varies inversely to that of said output of said radiation detector with changes in said ambient temperature.

13. A spectrophotometer according to claim 11, wherein said sixth means includes eight means for measuring said ambient temperature at a first instant of time, said first instant of time occuring immediately prior to a period when said first set of signals is generated or immediately subsequent to said period when said first set of signals is generated or during said period when said first set of signals is generated, ninth means for storing said ambient temperature measured at said first instant of time, and tenth means for measuring said ambient temperature at a second instant of time, said second instant of time occurring immediately prior to a period when said second set of signals is produced or immediately subsequent to said period when said second set of signals is produced or during said period when said second set of signal is produced, and wherein said seventh means modified said first or said second set of signals in accordance with a difference in ambient temperature between said first and second instants of time, said difference compensating for changes in sensitivity of said radiation detector with temperature.

14. A spectrophotometer according to claim 13, wherein said selected wavelength range for said first set of signals is equivalent to said second selected wavelength range for said second set of signals.

15. A spectrophotometer according to claim 13, wherein eleventh means are provided for displaying said transmittance or absorbance of said sample.

16. A spectrophotometer according to claim 13, wherein eleventh means are provided for converting transmittance or absorbance calculated by said fifth means into concentration for display.

17. A spectrophotometer according to claim 11, wherein said sixth means includes eighth means for measuring said ambient temperature at a first instant of time, said first instant of time occurring immediately prior to a period when said first set of signals is generated or immediately subsequent to said period when said first set of signals is generated or during said period when said first set of signals is generated, and ninth means for measuring said ambient temperature at a second instant of time, said second instant of time occurring immediately prior to a period when said second set of signals is produced or immediately subsequent to said period when said second set of signals is produced or during said period when said second set of signals is produced, and wherein said seventh means includes tenth means for modifying said first set of signals in accordance with a difference between said ambient temperature measured at said first instant of time and a predetermined temperature, and eleventh means for modifying said second set of signals in accordance with a difference between said ambient temperature measured at said second instant of time and said predetermined temperature.

18. A spectrophotometer according to claim 17, wherein said selected wavelength range for said first set of signals is equivalent to said second selected wavelength range for said second set of signals.

19. A spectrophotometer according to claim 17, wherein twelfth means are provided for displaying said transmittance or absorbance of said sample.

20. A spectrophotometer according to claim 17, wherein twelfth means are provided for converting transmittance or absorbance calculated by said fifth means into concentration for display.

21. A spectrophotometer according to claim 11, wherein said selected wavelength range for said first set of signals is equivalent to said second selected wavelength range for said second set of signals.

22. A spectrophotometer according to claim 11, wherein eighth means are provided for displaying said transmittance or absorbance of said sample.

23. A spectrophotometer according to claim 11, wherein eight means are provided for converting transmittance or absorbance calculated by said fifth means into concentration for display.

* * * * *